(12) United States Patent
Finley et al.

(10) Patent No.: US 8,445,037 B2
(45) Date of Patent: May 21, 2013

(54) VOLATILE DISTILLATE BY-PRODUCT OF MINT OIL THAT PROMOTES ABSORPTION AND/OR BIOAVAILABILITY OF COMPOUNDS OF BIO-MEDICAL AND NUTRITIONAL INTEREST

(75) Inventors: John Westcott Finley, Baton Rouge, LA (US); John Weldon Finley, Chalfont, PA (US); Igor Mezine, Malvern, PA (US); James M. Kehrer, II, Coloma, MI (US); Robert J. Justice, II, Portage, MI (US)

(73) Assignee: A. M. Todd Company, Kalamazoo, MI (US)

( * ) Notice: Subject to any disclaimer, the term of this patent is extended or adjusted under 35 U.S.C. 154(b) by 358 days.

(21) Appl. No.: 12/607,617

(22) Filed: Oct. 28, 2009

(65) Prior Publication Data
US 2010/0197801 A1 Aug. 5, 2010

Related U.S. Application Data

(60) Provisional application No. 61/108,953, filed on Oct. 28, 2008, provisional application No. 61/170,763, filed on Apr. 20, 2009.

(51) Int. Cl.
*A61K 36/53* (2006.01)

(52) U.S. Cl.
USPC .......................................................... 424/747

(58) Field of Classification Search
None
See application file for complete search history.

(56) References Cited

U.S. PATENT DOCUMENTS

| | | | |
|---|---|---|---|
| 2,662,052 A * | 12/1953 | Bridger et al. ................... | 203/44 |
| 4,495,033 A | 1/1985 | Rathbun et al. | |
| 4,861,616 A * | 8/1989 | Spencer ......................... | 426/651 |
| 5,030,459 A | 7/1991 | Barcelon et al. | |
| 5,240,932 A | 8/1993 | Morimoto et al. | |
| 5,425,962 A * | 6/1995 | Johnson et al. .................... | 426/3 |
| 5,665,386 A | 9/1997 | Benet et al. | |
| 5,665,690 A | 9/1997 | Lucas et al. | |
| 5,716,928 A | 2/1998 | Benet et al. | |
| 5,824,337 A | 10/1998 | Mullen | |
| 5,891,465 A | 4/1999 | Keller et al. | |
| 5,891,501 A * | 4/1999 | McKellip et al. .............. | 426/489 |
| 6,132,760 A | 10/2000 | Hedenstrom et al. | |
| 6,153,571 A | 11/2000 | Komocki et al. | |
| 6,300,377 B1 | 10/2001 | Chopra | |
| 6,342,208 B1 | 1/2002 | Hyldgaard et al. | |
| 6,616,942 B1 | 9/2003 | Udel | |
| 6,623,734 B2 | 9/2003 | Udell et al. | |
| 6,723,337 B1 | 4/2004 | Song et al. | |
| 6,740,338 B1 | 5/2004 | Chopra | |
| 6,806,069 B2 | 10/2004 | Chokshi | |
| 6,855,733 B2 | 2/2005 | Udell et al. | |
| 6,955,820 B1 | 10/2005 | Udell | |
| 7,026,361 B2 | 4/2006 | Minemura et al. | |
| 7,030,102 B1 | 4/2006 | Madhavi et al. | |
| 7,060,263 B2 | 6/2006 | Udell et al. | |
| 7,094,804 B2 | 8/2006 | Behnam | |
| 7,273,606 B2 | 9/2007 | Fantuzzi et al. | |
| 7,273,622 B2 | 9/2007 | Udell et al. | |
| 7,438,903 B2 | 10/2008 | Parkhideh | |
| 2003/0044474 A1 | 3/2003 | Tao et al. | |
| 2004/0033254 A1 | 2/2004 | Song et al. | |
| 2004/0127531 A1 | 7/2004 | Lu et al. | |
| 2004/0152612 A1 | 8/2004 | Supersaxo et al. | |
| 2005/0037066 A1 | 2/2005 | Udell et al. | |
| 2005/0169988 A1 | 8/2005 | Tao et al. | |
| 2005/0181031 A1 | 8/2005 | Saito et al. | |
| 2005/0192199 A1 | 9/2005 | Cartwright et al. | |
| 2006/0165622 A1 * | 7/2006 | Hiramoto et al. ................ | 424/65 |

FOREIGN PATENT DOCUMENTS

JP 2002038187 * 2/2002

OTHER PUBLICATIONS

Schantz et al. Italiana Essenze, Profumi, Piante Officinali—Aromi Saponi Cosmetici Aerosol. 1973. vol. 55, No. 9, pp. 565-571.*
McKay, D.L. and Blumberg, J.B. A Review of the Bioactivity and Potential Health Benefits of Peppermint Tea (Mentha piperita L.) Phyother. Res 20(8):619-633, 2006.
Littarru, G.P. and Langsjoen,P. "Coenzyme Q10 and statins: biochemical and clinical implications" Mitochondrion.7 Suppl:S168-S174, 2007.
Okello, Emmy,Jiang, X., Motiameo, S., Mohamed, S., Zhao, Q., Wang. T. "Combined statin/coenzyme Q10 as adjunctive treatment of chronic heart failure", Med.Hypotheses 73 (3):306-308, 2009.
Kris-Etherton, P.M., Hecker, K.D., Bonanome, A, Coval, S.M., Binkoski A.E., Hilpert, K.F., Griel, A.E., Etherton, T.D. Bioactive compounds in foods; their role n the prevention of cardiovascular disease and cancer. Am. J. Med 113 Suppl. 9B:715-88S, 2002.

(Continued)

*Primary Examiner* — Chris R Tate
(74) *Attorney, Agent, or Firm* — Thaddius J. Carvis

(57) ABSTRACT

Disclosed is an adjuvant for improving the bioavailability of bioactive compositions. The adjuvant is prepared from a byproduct of mint flavor production. In vitro and in vivo testing confirms effectiveness. The adjuvant contains a mixture of compounds which is effective to improve the oral bioavailability of a bioactive composition normally having limited absorptivity, and it comprises a mixture of nonpolar compounds and compounds with some polar characteristics. In preferred form the nonpolar compounds comprise compounds selected from a group that includes terpene hydrocarbons and terpene derivatives and the compounds with some polar characteristics comprise compounds selected from a group that includes aldehydes, alcohols and ketones. The preferred compositions will have a ratio of nonpolar compounds and compounds with some polar characteristics is within the range of from 5:1 to 20:1. The adjuvants can enhance delivery of CoQ10 and other bioactive compositions, such as carotenoids (e.g., β-carotene), curcuminoids, lycopene, resveratrol, flavonoids and other phenolic compounds, organosulfur compounds, saponins, sterols, stanols, and mixtures of at least two of these, to the interior cellular environment, including organelles, such as the mitochondria.

9 Claims, 7 Drawing Sheets

OTHER PUBLICATIONS

Songkro, S., Rades, T., Becket, G. "Effects of some terpenes on the in vitro permeation of LHRH through newborn pig skin", Pharmazie 64 (2):110-116, 2009.

Dragicevic-Curic, N., Grafe, S., Albrecht, V., Fahr, A. Topical application of temoporfin-loaded invasomes for photodynamic therapy of subcutaneously implanted tumours in mice: A pilot study. J. Photochem, Photobiol. B91 (1):41-50, 2008.

Tas, C., Ozkan, Y., Okyar, A., Savaser, A. "In vitro and ex vivo permeation studies of etodolac from hydrophilic gels and effect of terpenes as enhancers", Frug Deliv. 14(7):453-459, 2007.

Nokhodchi, A., Sharabiani, K., Rashidi, M.R., Ghafourian, T. The effect of terpene concentrations on the skin penetration of diclofenac sodium, Int. J. Pharm. 335 (1-2):97-105, 2007.

Das, M.K., Bhattacharya, A., Ghosal, S.K. "Effect of different terpene-containing essential oils on percutaneous absorption of trazodone hydrochloride through muse epidermis." Drug Deliv. 13 (6):425-431, 2006.

Cal, K. Skin penetration of terpenes from essential oils and topical vehicles. Planta Med. 72 (4):311-316, 2006.

Nielsen, J.B. Natural oils affect the human skin integrity and the percutaneous penetration of benzoic acid dose-dependently. Basic Clin. Pharmacol. Toxicol. 98(6):575-581, 2006.

Cal, K., Sznitowaka, M., Cutaneous absorption and elimination of three acyclic terpenes—in vitro studies. J. Controlled Release 93 (3):369-376, 2003.

Yamane, M.A., Williams, A.C., Barry B.W. Terpene penetration enhancers in propylene glycol/water co-solvent systems: effectiveness and mechanism of action. J. Pharm.Pharmacol. 47 (12A):978-989,1995.

Obata, Y., et al., Effect of cyclic monoterpenes on percutaneous absorption in the case of a water-soluble drug (diclofenac sodium), 1990.

Okamoto, H., Ohyabu, M., Hashida, M., Sezaki, H. Enhanced penetration of mitomycin c through hairless muse and rat skin by enhancers with terpene moieties. J. Pharm. Pharmacol. 39 (7):531-534, 1987.

Vallette, G., et al. "Percutaneous absorption of the hydrocarbons of the benzene, cycloalkene, cycloalkene and terpend series", Therapie 7(2)139-143), 1952.

Dewitt, C., Bebarta, V. Botanical solvents. Clin Occup. Environ. Med 4 (3):445-4vi, 2004.

Mally, A., Chipman, J.K. "Non-genotoxic carcinogens: early effects on gap junctions, cell proliferation and apoptosis in the rat" Toxicology 180 (3):233-248, 2002.

Heuman, D.M. "Quantitative Estimation of the Hydrophilic—Hydrophobic balance of mixed bile salt solutions", J. Lipid Res. 30(5):719-730, 1989.

Press, R.R., Buckle, T. Beijnen, J.H., Van Tellingen, O., The effect of P-glycoprotein and cytochrome P450 3a on the oral bioavailability of vinorelbine in mice. Cancer Chemother Pharmacol 57 (6):819-825, 2006.

Press, B., et al "Permeability for intestinal absorption: Caco-2 assay and related issues" Curr. Drug Metab 9 (9):893-900) 2008.

Ochoa, J.J., Quiles, J.L., Lopez-Frias, M., Huertas, J.R., Mataix, J. "Effect of Lifelong Coenzyme Q10 Supplementation on Age-Related Oxidative Stress and Mitochondrial Function in Liver and Skeletal Muscle of Rats Fed on a polyunsaturated Fatty Acid (PUFA)-Rich Diet" J. Gerontol, A.Biol.Sci. 6A(11):1211-1218, 2007.

Kelso, G., Porteous, C.M., Hughes G., Ledgerwood, E.C., Gane, A.M., Smith, R. A.J., Murphy, M.P. "Prevention of Mitochondrial Oxidative Damage Using Targeted Antioxidants," Ann.N.Y.Acad. Sci. 959:263-274, 2002.

Nelson, S.D.,"Mechanisms of the formation and disposition of reactive metalolites that can cause acute liver injury" Drug Metal Rev. 27 (1&-2);147-177), 1995.

Turunen, M., Appelkvist, E.L., Sindelar, P., Daliner, G. "Blood Concentration of Coenzyme Q10 Increases in Rats When Esterified Forms are Administered", J.Nutr. 129(12):2113-2118, 1999.

Cal, K. "Skin Penetration of terpenes fron essential oils and topical vehicles". Planta Med. 72(4):311-316, 2006.

Yamane, M.A., Williams, A.C., Barry B.W. "Terpene penetration enhances in propylene glycol/water co-solvent systems: effectiveness and mechanism of action". J. Pharm Pharmacol. 47(12A):978-989, 1995.

Okamoto, H., Ohyabu, M., Hashida, M. Sezaki, H. "Enhanced penetration of mitocycin through hairless mouse and rat skin by enhancers with terpene moieties". J. Pharm. Pharmacol. 39(7):531-534, 1987.

Valette, G., Cavier, R. "Percutaneous absorption of the hydrocarbons of the benzene, cycloalkane, cycloalkene and terpene series", Therapie 7(2):139-143, 1952.

Press, B., Di Grandi, D., "Permeability for intestinal absorption: Caco-2 assay and related issues", Curr. Drug Metab (9):893-900, 2008.

Obata, Y., Takayama, K., Okabe, H., Nagai, T., Effect of cyclic monoterpenes on percutaneous absorption in the case of a water-soluble drug (diclofenac sodium), Drug Design and Delivery, (6):319-328, 1990.

\* cited by examiner

Uptake of CoQ10 by Caco-2 is dependent on the concentration of VDMO in serum-free experimental medium.

Transport of CoQ10 across a monolayer of Caco-2 cells is dependent on the concentration of VDMO in serum-free experimental medium. The effect of treatment is significant at $p<0.0001$ by ANOVA; Values are Means+SEM; different superscripts represent means significantly different from each other.

Transport of CoQ10 across a monolayer of Caco-2 cells is dependent on the concentration of VDMO in experimental medium containing serum. The effect of treatment is significant at p<0.0003 by ANOVA; Values are Means+SEM; different superscripts represent means significantly different from each other.

The kinetics of CoQ10 appearance in the serum appears to be altered by the amount of VDMO mixed into the emulsion. Each point is the mean of five measurements from different mice; data were not statistically analyzed.

The ratio of VDMO:CoQ10 alters the concentration of CoQ10 in the sera of mice gavaged for four consecutive days.

The ratio of VDMO:CoQ10 alters the concentration of CoQ10 in the sera of mice gavaged for nine consecutive days, as compared to CoQ10 mixed in an aqueous solution or CoQ10 mixed with soybean oil.

The ratio of VDMO:CoQ10 alters the concentration of CoQ10 in the mitochondria of the liver of mice administered CoQ10 by gavage for nine consecutive days.

VOLATILE DISTILLATE BY-PRODUCT OF MINT OIL THAT PROMOTES ABSORPTION AND/OR BIOAVAILABILITY OF COMPOUNDS OF BIO-MEDICAL AND NUTRITIONAL INTEREST

RELATED APPLICATIONS AND PRIORITY CLAIM

This application claims priority to U.S. Patent Provisional Applications 61/108,953, filed Oct. 28, 2008 and 61/170,763, filed Apr. 20, 2009, having the same title as above. Both of these applications are incorporated herein in their entireties.

FIELD OF THE INVENTION

The invention relates generally to enhancing the bioavailability of many bioactive substances, and in particular to a volatile distillate by-product of mint oil (VDMO), prepared from the essential oils of mint and containing a mixture of polar and nonpolar compounds, which possess beneficial solubility characteristics for poorly bioavailable compositions that impart health benefits (e.g., Coenzyme Q10 (ubiquinone; CoQ10), carotenoids (e.g., β-carotene), curcuminoids, lycopene and resveratrol), the methods of their manufacture and application of the preparations for enhancing bioavailability of certain bioactive substances.

BACKGROUND OF THE INVENTION

Because the invention, which largely solves the problem of enhancing the bioavailability of some bioactive compositions, is based on mint extract byproducts, we start our discussion by providing some background on mint extraction before explaining the nature of the problems solved by the invention.

Mint flavoring has been used in some medications and mint has often been associated with soothing foods, but mint has not been proposed as an adjuvant for bioactive compositions as we have found for a particular fraction of the extracted oils which is freed of most of the mint flavoring compounds.

The mint family of herbs, botanical family name Labiatae, encompasses multiple genera including *Rosmarinus* (rosemary), *Monarda* (horsemint) and *Mentha* (mint). Common mint species include *Mentha piperita* (peppermint), *Mentha spicata* (spearmint), *Mentha arvensis* (corn mint) and *Mentha pulegium* (pennyroyal). Mint species are well known for the aromatic volatile essential oils in their foliage. Methods of distillation for extraction and refining of the essential oils for use for their aroma or flavor characteristics in perfumes, flavorings and medicines have long been established. Some of the fractions separated are highly desired, and some are extracted due to their tendency to dilute or alter the more desired flavor compositions.

Mint teas comprised of the entire mint leaf, including cellular components and molecules in addition to the essential oils, have been consumed as food and medicine for many centuries. Mint is claimed to be effective for the reduction of digestive disorders including colic, indigestion, nausea, and stomach cramps and reduction of severity of symptoms from Irritable Bowel Syndrome (McKay, et al. (2006) "*A review of the bioactivity and potential health benefits of peppermint tea (Mentha piperita L.)*" Phytother. Res. 20 (8):619-633, 2006).

Methods have long been available for the separation of volatile organics from plant material and for the further purification of those oils. Most techniques are in the public domain, and a few are the subjects of patents. For example, Rathbun and Thalheimer described a continuous method for separating volatile organic components from fibrous plant material in U.S. Pat. No. 4,495,033. Further separation of distinct volatile components has been described; e.g., Barcelon, et al., described a method for further purification of mint flavor for the production of high-impact chewing gum (U.S. Pat. No. 5,030,459).

Only a small fraction of low-boiling mint compounds are used in the production of flavors/aromas, and the low boiling fractions are often considered byproducts. Owing to the traditionally recognized solvent capabilities of essential oils, low-boiling fractions of flavor oils are often sold as cleaning agents. For example, a distillation method for producing a cleaning product composed of a high percent of terpenes is described by Komocki, et al., in U.S. Pat. No. 6,153,571 and a low-toxicity cleaning solvent compound composed primarily of monoterpenes is described by Lucas, et al., in U.S. Pat. No. 5,665,690. Essential oils are also a component of a cleaner described in U.S. Patent Publication No. 2005/0192199 A1, to Cartwright, et al.

Mint oils are complex essential oils composed of many diverse individual chemicals that range from hydrophilic to lipophilic. Mint oils have been utilized in food for many centuries and mint oils are Generally Recognized As Safe (GRAS) by the U.S. FDA. Mint flavoring has been used in some medications and mint has often been associated with soothing foods, but mint has not been proposed as an adjuvant for bioactive compositions despite the fact that there are significant needs for adjuvants to facilitate the use of bioactives in the treatment of numerous medical conditions and maladies facing mammals, especially modern man.

Heart disease, diabetes and cancer are major health care problems facing the U.S. and many other Westernized countries. Today, the total annual health care cost for Cardio Vascular Disease (CVD) in the U.S. is expected to be more than $431 billion, and the cost for cancer is expected to exceed $200 billion. Additionally, the total annual cost for diabetes in the U.S. is estimated to be $100-150 billion.

A primary class of drugs used for the reduction of serum cholesterol levels, and subsequent reduction of CVD risk are the statins, however, statins inhibit the formation of farnesyl pyrophosphate, an intermediate in the biosynthesis of Coenzyme Q10 (ubiquinone; CoQ10). CoQ10 is utilized in the mitochondria for energy production. Deficiency of CoQ10 induced by statins may be the cause of 'statin-¬induced myopathy', an often-noted lethargy and malaise associated with statin consumption (Littarru et al. (2007 "*Coenzyme Q10 and statins: biochemical and clinical implications*" Mitochondrion. 7 Suppl:S168-S174). Consequently many health care practitioners urge CoQ10 supplementation concomitant with statin use (Okello et al. (2009) "*Combined statin/coenzyme Q10 as adjunctive treatment of chronic heart failure*" Med. Hypotheses 73 (3):306-308). However, the bioavailability (defined as the product of absorption from the intestine as well as the utilization of the specific compound by the target tissue) of CoQ10 is quite low, and oral consumption of CoQ10 may have limited effectiveness.

Resveratrol (trans-3,5,4'-trihydroxystilbene) and lycopene (2,6,10,14,19,23,27,31-octamethyldotriaconta-2,6,8,10,12, 14,16,18,20,22,24,26,30-tridecaene) are compounds found in red wine and tomatoes, respectively, that may be protective against chronic disease (Kris-Etherton et al., (2002) "*Bioactive compounds in foods: their role in the prevention of cardiovascular disease and cancer*" Am. J. Med. 113 Suppl 9B:71S-88S). Increasing evidence suggests that consumption of resveratrol may be protective against heart disease and lycopene may be protective against prostate cancer. Both compounds may function as an antioxidant, anti-inflammatory agent or by other pathways, but most nutritionists agree that the in vivo significance of these compounds also is limited because poor absorption results in limited bioavailability.

There are many other substances capable of benefiting human health but are of questionable benefit because of limited bioavailability. Their poor absorption is possibly related to difficulty to keep them in solution in the absorptive area of the gut. Overcoming problems with bioavailability could open up many possibilities for reducing the risk of chronic disease by inclusion of these and similar compounds in foods, dietary supplements and/or drugs.

Dermal bioavailability is a relatively simple process that is primarily a function of penetration across the various dermal layers, whereas oral bioavailability is considerably more complex; a function of diffusion across the unstirred water layer, active and passive transport into and out of the absorptive cell, hepatic metabolism and re-excretion into the G.I. tract.

There is evidence that dermal penetration of hydrophobic drugs is enhanced by certain naturally-derived compositions. For example, co-administration of hydrophobic drugs with terpene mixtures has shown some promise. See, for example, Songkro, S., et al. (2009) "*Effects of some terpenes on the in vitro permeation of LHRH through newborn pig skin*" Pharmazie 64 (2):110-115; N. Dragicevic-Curic, N., et al. (2008) "*Topical application of temoporfin-loaded invasomes for photodynamic therapy of subcutaneously implanted tumours in mice: a pilot study*" J. Photochem. Photobiol. B 91 (1):41-50; Tas, C., et al., (2007) "*In vitro and ex vivo permeation studies of etodolac from hydrophilic gels and effect of terpenes as enhancers*" Drug Deliv. 14 (7):453-459; Nokhodchi, A. et al. (2007) "*The effect of terpene concentrations on the skin penetration of diclofenac sodium*" Int. J. Pharm. 335 (1-2):97-105; Das, M., et al. (2006) "*Effect of different terpene-containing essential oils on percutaneous absorption of trazodone hydrochloride through mouse epidermis*" Drug Deliv. 13 (6):425-431; Cal, K. (2006) "*Skin penetration of terpenes from essential oils and topical vehicles*" Planta Med. 72 (4):311-316; Nielsen, J., (2006) "*Natural oils affect the human skin integrity and the percutaneous penetration of benzoic acid dose-dependently*" Basic Clin. Pharmacol. Toxicol. 98 (6):575-581; Cal, K. et al., (2003) "*Cutaneous absorption and elimination of three acyclic terpenes—in vitro studies*" J. Control Release 93 (3):369-376; Yamane, M., et al. (1995) "*Terpene penetration enhancers in propylene glycol/water co-solvent systems: effectiveness and mechanism of action*" J. Pharm. Pharmacol. 47 (12A):978-989; Obata, Y. et al. (1990) "*Effect of cyclic monoterpenes on percutaneous absorption in the case of a water-soluble drug (diclofenac sodium)*" Drug Des Deliv. 6 (4):319-328; Okamoto, H. et al., (1987) "*Enhanced penetration of mitomycin C through hairless mouse and rat skin by enhancers with terpene moieties*" J. Pharm. Pharmacol. 39 (7):531-534; Vallette, G. et al. (1952) "*Percutaneous absorption of the hydrocarbons of the benzene, cycloalkane, cycloalkene and terpene series*" Therapie 7 (2):139-143). Multiple patents exist for dermal delivery systems that include terpenes (U.S. Pat. No. 6,342,208 to Hyldgaard et al.; U.S. Pat. No. 6,132,760 to Hendenstrom et al. Oct. 17, 2000; U.S. Pat. No. 6,723,337 to Song et al.; U.S. Pat. No. 5,240,932 to Morimoto, et al.; and patent publications (2004/0127531 to Lu, et al.; U.S. Patent Publication No. 2004/0033254 to Song, et al.; 2005/0181031 to Saito, et al.) also exist for dermal applications that use extracts or absolutes from plant species that contain terpenes. The increased dermal bioavailability of the above compounds is most likely solely a result of the ability of terpenes to effectively dissolve and keep in solution the compound of interest.

The more complex process of oral bioavailability demands studies that specifically address the process.

Numerous attempts have been made to improve the oral bioavailability of molecules such as CoQ10, especially by formulations that increase the solubility of the CoQ10. CoQ10 has been formulated with various lipids including rice bran oil provided in a soft gel capsule (U.S. Pat. Nos. 6,955,820 and 6,616,942 to Udell, and U.S. Pat. Nos. 7,060,263 B-2, 6,623,734 and 7,273,622 to Udell, et al.), various lipids used to form preliposomes (U.S. Patent Publication No. 2005/0037066 to Chen, et al.) and liposomes (U.S. Pat. No. 5,891,465 to Keller, et al.), various lipids (U.S. Pat. No. 6,855,733 to Udell, et al.), emulsifications with various lipids (U.S. Pat. No. 7,094,804 to Behnam et al.; U.S. Patent Publication No. 2004/0152612 A1 to Supersaxo et al), various lipids and triglycerides (U.S. Patent Publication Nos. 2005/0169988 A1 and 2003/0044474 A1 to Tao, et al.), glyceryl esters (U.S. Pat. No. 6,300,377 to Chopra) and emulsifications including organic acids (U.S. Pat. No. 7,026,361 to Minemura, et al.). Additionally the reduced form of CoQ10 (ubiquinol) has been used in preparations with various lipids (U.S. Pat. No. 6,740,338 to Chopra). Non-lipid approaches to increasing the bioavailability of CoQ10 include bacterial and yeast fermentation in the presence of CoQ10 as described by Chokshi in U.S. Pat. No. 6,806,069 B2, and complexing CoQ10 with cyclodextrin (U.S. Pat. No. 7,030,102) and production of nanoscale CoQ10 in a lipid matrix (U.S. Pat. No. 7,438,903 to Parkhideh, et al.). Most of the solvents utilized are common food grade lipids; however, few food grade lipids function well as solvents of CoQ10 and improvements of bioavailability, if reported, are modest at best.

A method for increasing the bioavailability of CoQ10 by solubilization in d-limonene is disclosed in U.S. Pat. No. 7,273,606 to Fantuzzi, et al. The patent states that CoQ10 can be readily dissolved in the monoterpene d-limonene, a primary component of essential oils isolated from lime, and to a much lesser extent, mint. Limonene is GRAS for use as a flavoring agent, however very small amounts are used as flavors and greater amounts are needed to improve bioavailability of bioactive molecules. Although the data are inconclusive, there are toxicity concerns, including cancer, with d-limonene (DeWitt, C. et al. (2004) "*Botanical solvents*" Clin. Occup. Environ. Med. 4 (3):445-4vi; Mally, A., et al. (2002) "*Non-genotoxic carcinogens: early effects on gap junctions, cell proliferation and apoptosis in the rat*" Toxicology 180 (3):233-248). Thus, the total intake of limonene needed for enhancement of bioavailability of bioactive molecules may make it unsuitable for most oral applications, especially for substances that may be ingested on a daily basis over a prolonged period.

Fantuzzi, et al., (U.S. Pat. No. 7,273,606) assert that limonene, and monoterpenes in general, are responsible for solubilizing CoQ10, and that solubilization in turn increases CoQ10 bioavailability. In the body, bile salts are the physiologic mechanism for emulsification and subsequent absorption of fats. However, the effectiveness of bile salts is a result of their amphiphilic nature; i.e., they possess both hydrophilic and lipophilic characteristics (Heuman (1989) Heuman, M. *Quantitative estimation of the hydrophilic-hydrophobic balance of mixed bile salt solutions*. J. Lipid Res. 30 (5):719-730. Limonene appears to function solely as a solvent of hydrophobic molecules.

Benet, et al., teach that essential oils when co-administered with a pharmaceutical compound can increase the bioavailability of that compound (U.S. Pat. Nos. 5,716,928 and 5,665,386 to Benet, et al.). Further, Benet, et al., uses the term "pharmaceutical compound" to encompass, among others, quinone compounds, and Benet, et al., include oils of peppermint and spearmint in their universe of essential oils. However, Benet, et al., teach that increased bioavailability is a function of (in addition to other factors) metabolism of the compound and that bioavailability may be enhanced when metabolic transformations are inhibited. To that end, they have established as a criterion for enhancing bioavailability, the ability of an oil to inhibit conversion of cyclosporine to hydroxylated products, and in general to inhibit enzymes of the cytochrome P450 3A class. Further Benet et al. have provided data showing inhibition of cyclosporine transformation as evidence for increases in bioavailability.

Mullen, in U.S. Pat. No. 5,824,337 is directed to provision of economical micelles and micelle-like structures which can be used as carriers for protection of substances which are lipids or lipophilic or are soluble or easily dispersed in oils or other lipid-like compounds. Examples of such substances are said to include drugs which are lipophilic such as immunogens or steroids, fragrances, flavorings and nutrients. One example shows that micellular solutions can be made with the oils from mint. However numerous substances capable of producing micelles are not capable of dissolving CoQ10 as well as other lipophilic molecules. Moreover, the substances comprising the micelle itself may interfere with metabolism of the bioactive resulting in even decreased bioavailability. Therefore the ability of crude mint oil to form micelles does not demonstrate dissolution of CoQ10 within the micelle nor does it demonstrate increased absorption and/or decreased metabolism of CoQ10.

Biological systems are complex, and isolation of one component does not teach the function of the system as a whole. Benet, et al., teach that peppermint and spearmint oil are among the essential oils that inhibit cytochrome P450 3A, and from this they assume bioavailability is enhanced. Without a direct measure of absorption/bioavailability, however it is not immediately obvious that the one action results in the second outcome. Indeed, Press, R., et al., (2006; "*The effect of P-glycoprotein and cytochrome P450 3a on the oral bioavailability of vinorelbine in mice*" Cancer Chemother. Pharmacol. 57 (6):819-825) reported that substantial inhibition of cytochrome P450 3A resulted in only a minimal change in the oral bioavailability of vinorelbine in mice. Therefore, it is essential that claims of increased bioavailability be documented by specific measures of such, rather than inferred from isolated processes. Thus, the teaching of Benet does not teach an actual increase in absorption and/or bioavailability of any compound.

Because we have found that a byproduct mint oil fraction has strong adjuvant properties, we note that there are many reasons why raw mint oil is not suitable as a solvent system for the adjuvant purposes. Raw unfractionated mint oil would require too large a dose for inclusion in many dietary supplement and pharmaceutical applications. In order to be suitable for galenical development of these delivery forms, it must be fractionated and extraneous fractions must be eliminated. Raw mint oil also contains substances which may be unsafe in larger doses (e.g., limonene, pulegone), these too must be reduced or eliminated. Moreover, an adjuvant should not have an overpowering flavor that makes consumption of effective amounts difficult.

In vitro measures of bioavailability are often conducted by using Caco-2 cells, a cell line that is recognized by the food and pharmaceutical industry as an excellent in vitro screen to determine potential oral bioavailability. (Press, B. et al. (2008) "*Permeability for intestinal absorption: Caco-2 assay and related issues*" Curr. Drug Metab 9 (9):893-900) Caco-2 cells are cells derived from a human colon cancer malignancy. If properly maintained, the cells will remain alive indefinitely (i.e. they are immortal), but when grown under correct conditions they can be "transformed" into a cell type that grows to maturity then dies (thus mimicking the way most cells in the body grow). Interestingly, during this transformation the cells transform into a cell almost identical to the absorptive area of the small intestine, and this quality has made the Caco-2 cell line the method of choice for studies of processes that occur in the gut; e.g., absorption.

Absorption of a substance involves two distinct mechanisms—first, the substance must be taken up from the lumen of the gut and enter the absorptive cell, and second, the substance must be excreted from the absorptive cell into the lymph or blood on the serosal side of the cell. A test substance can be added to the medium in which the cells are grown, then the cells can be separated from the medium and the amount of substance that is taken up into the cell can be measured. Additionally, if Caco-2 cells are grown on a porous membrane at the bottom of a small plastic cup, the cells will interlock in 'tight junctions' with neighboring cells, resulting in a confluent, water-tight monolayer of cells. This insert can then be placed in a solid well and media put inside the insert (on the apical side of the cells, or the side corresponding to the gut lumen) and in the well (on the basolateral side of the cell or the side corresponding to the serosa of the body). Substances added to the top (apical) side of these cells can only pass to the bottom by being taken up into the cell and then transported (or diffused) out the bottom (basolateral side). Such a system gives a very reliable indication of whether, and to what extent, absorption is taking place; hence an indication of 'bioavailability'.

Rodent animal studies give a more reliable measure of bioavailability. Increased concentration of the metabolite of interest in the plasma or serum is an accepted measure of bioavailability. However, increased serum concentrations are not necessarily definitive proof that the concentration of the metabolite increases in the tissue (and/or sub-cellular compartment) of interest. CoQ10 is needed for energy production and thus is needed in the mitochondria of tissues that utilize a great amount of energy; the mitochondria of the heart and liver are such tissues (Ochoa, J. et al. (2007) "*Effect of lifelong coenzyme Q10 supplementation on age-related oxidative stress and mitochondrial function in liver and skeletal muscle of rats fed on a polyunsaturated fatty acid (PUFA)-rich diet*" J. Gerontol. A Biol. Sci. Med. Sci. 62 (11):1211-1218; Kelso, G. et al. (2002) "*Prevention of mitochondrial oxidative damage using targeted antioxidants*" Ann. N.Y. Acad. Sci. 959: 263-274).

There is a present need for methods and compositions effective for enhancing the bioavailability of poorly bioavailable compositions that impart health benefits such as Coenzyme Q10 (ubiquinone; CoQ10), carotenoids (e.g., β-carotene), curcuminoids, lycopene and resveratrol.

SUMMARY OF THE INVENTION

It is a primary object of the invention to provide adjuvant compositions that improve the oral bioavailability of bioactive compositions which normally have such limited solubility that they are not effectively utilized in mammalian bodies.

It is another object of the present invention to provide novel compositions derived from the mint distillates comprising essential oils of mint.

It is a more specific object of the invention to provide an adjuvant for bioactive compositions like CoQ10 and similar compositions, which have their strong functionality limited by their poor oral solubility and consequent limited oral bioavailability.

It is another specific object of the invention to provide advantages of a biochemical import while improving agricultural efficiency by utilizing portions of mint oil that might otherwise be disposed of.

DETAILED DESCRIPTION OF THE INVENTION

Figure 1:
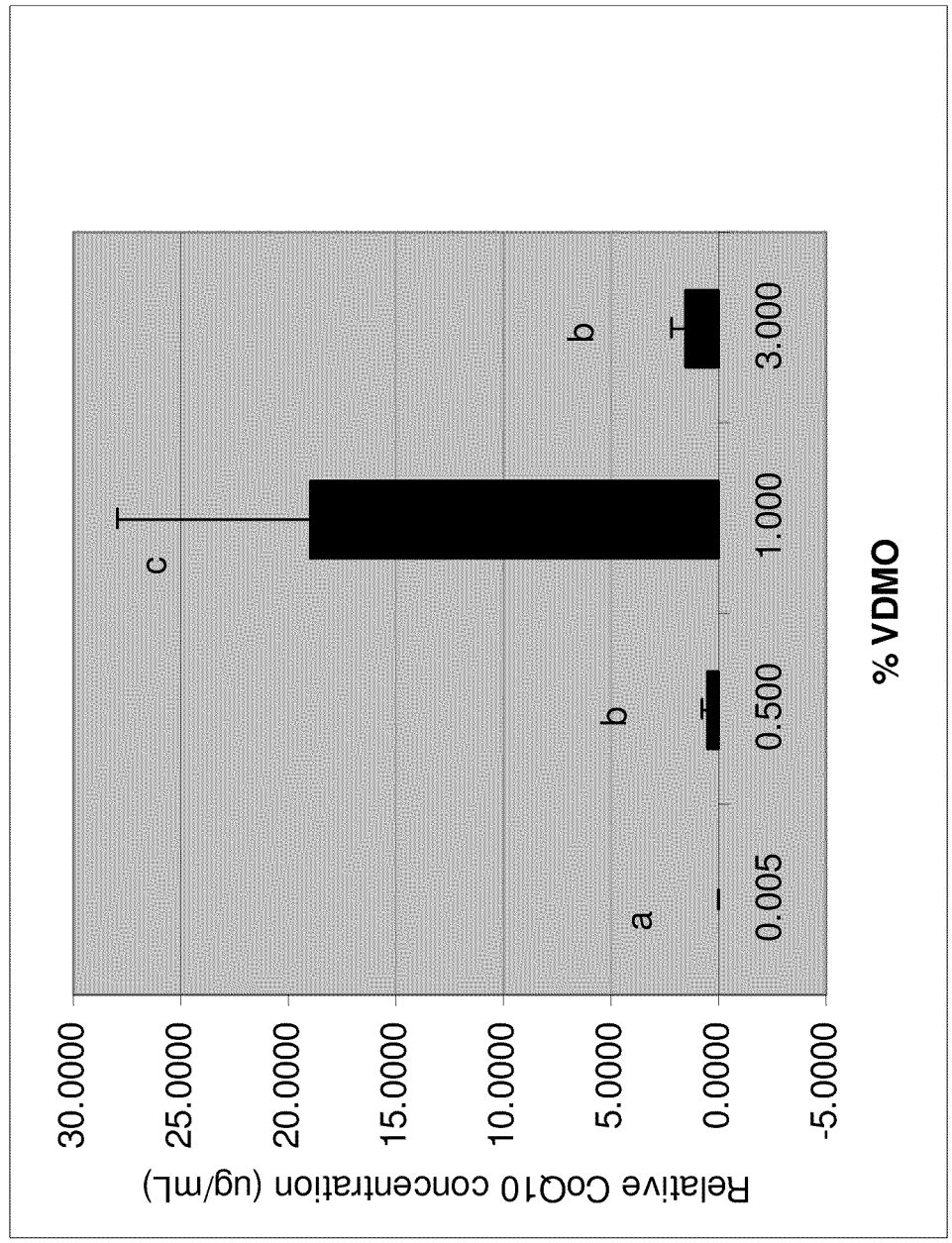
FIG. 1 is a graph showing that VDMO resulted in a statistically-significant, dose-dependent change in the uptake of CoQ10 by CACO-2 cells in media that did not contain serum.

The invention relates generally to adjuvant compositions having the ability of enhancing the bioavailability of certain bioactive compositions.

In the context of the invention, the term "adjuvant" includes any substance that enhances the biochemical effect of a bioactive composition in mammals, particularly humans. In the context below, we take evidence of increased absorption as evidence of enhanced biochemical effect.

By the terms "bioactive composition" we intend to include all compositions, including individual compounds and mixtures of compounds, which are bioactive.

The term "bioactive" in the context of the invention means that the composition in question has some measurable effect on one or more of the following indicators: physiologic outcomes, such as a change in blood pressure; clinical measures, such as a change in cholesterol; metabolic processes, such as a change in antioxidant tone; molecular processes, such as decreased protein or DNA damage; genetic processes, such as activation of cytokine pathways or specific genes.

The term "increased absorption" in the context of the invention means that a specified bioactive composition or mixture of such will be absorbed into the body and transported to the blood of a mammal to a statistically-significantly greater extent than would occur without the adjuvant of the invention. We describe both in vitro and in vivo methodology to evidence absorptivity. Other tests may also be useful so long as there is evidence correlating the test results to mammalian absorptivity. In a practical measure of increased absorption, we take an increase of at least 10% as a meaningful improvement; however, there is no actual lower limit, and the invention is intended to include increases of any measurable level. Preferred increases will be at least 25%, and improvements of 50% and more can be highly beneficial. By improving absorption of bioactive compositions, the invention improves their bioavailability.

The adjuvant compositions provided by the invention as described herein are prepared as byproducts of mint flavor manufacture and incorporate large amounts of natural constituents of mint that have little or no mint flavor, but may still contain some important mint flavor components in minor amounts. In its preferred form, the adjuvant of the invention is a volatile distillate by-product of mint oil (VDMO), prepared from the distilled fraction of mint extract containing the essential oils of mint. It is a fraction remaining after the most desired mint flavor compounds are extracted. In preferred forms it will be found to contain a mixture of nonpolar compounds and compounds with some polar characteristics, which possess beneficial solubility characteristics for hydrophobic molecules that impart health benefits (e.g., Coenzyme Q10 (ubiquinone; CoQ10), β-carotene, lycopene, resveratrol), the methods of their manufacture and application of the preparations for enhancing bioavailability of bioactive compositions that are characterized by a poor absorptivity due at least in part to solubility in the gut and/or transport from the gut into the blood. There are many other substances capable of benefiting human health but are of questionable benefit because of limited bioavailability.

Some bioactive compositions are poorly absorbed because they are not soluble in oils or water—making it difficult to keep them in solution in the absorptive area of the gut. Such compounds do not cross the unstirred water layer in the gut lumen and come in contact with the absorptive region of the gut epithelia, either alone or as a component of a lipid micelle. In effect, the adjuvant of the invention is believed to act as a solvent capable of dissolving the compositions of interest and facilitating their movement to the gut epithelium, thereby improving their bioavailability. Advantageously, the invention provides oil solubilization characteristics for the initial dissolution, and also water solubilization characteristics for the formation of micelles and facilitated transport through the lumen. It is an advantage of the present invention that bioavailability of many compositions can be improved, which can open up many possibilities for reducing the risk of chronic disease by inclusion of these normally poorly absorbed compositions in foods, as dietary supplements and/or as drugs. The VDMO compositions of the invention contain both polar and nonpolar compounds and are believed to function in a manner more similar to bile salts than do solutions of pure solvents, such as limonene.

Typically, the production of a mint flavor involves steam distillation of dried hays of a suitable mint species (e.g., *Mentha piperita*) in the field to separate a crude volatile component from fibrous plant material. The resultant crude oil may be used directly in some applications, but the production of high-quality flavors may require further refinement. This is typically accomplished by exposure of the crude oil to indirect heat under vacuum conditions. As often conducted this process meets the purpose of removing compounds that volatilize at relatively low temperatures because such compounds often impart 'off' odors or taste. Such a separation is accomplished by a gradient of nominal process heat in the distillation column, resulting in the separation of the low-boiling components from other higher boiling fractions that contain the compounds of interest to flavor producers. The low-boiling fraction of mint oils consists of terpene hydrocarbons, the oxygenated terpene 1,8-cineole, various aldehydes (2- and 3-methylbutanal, 2-methylpropanal, etc.), alcohols, ketones, and alkanes.

As is known, mint oils are typically produced by cutting mint plants at a proper maturity and allowing them to partially dry and form mint hay. In the normal course, the mint hay is then subjected to a field-based steam distillation process that recovers the majority of the volatile organic compounds. Higher-quality and specialized mint flavor often require subsequent re-distillation, such re-distillation produces fractions with different compositions and properties. Quite often, this redistillation requires removal of the fractions that volatilize at lower temperatures, and much of these fractions become a residual byproduct. The present invention provides a volatile distillate fraction of mint oil (VDMO) that comes from the fractions of mint oil that have been removed as byproducts during the process to make specialized and high-quality mint flavors.

While the prior art, such as Fantuzzi, et al., (U.S. Pat. No. 7,273,606) has taught that limonene is effective in increasing CoQ10 bioavailability, we have found that limonene is not important in the case of our mint oil fraction. Indeed, the distillation method of the present invention results in a mixture of essential oils with a low concentration (<5.0%) of limonene and pulegone (<0.15%) but is very effective in increasing the bioavailability of CoQ10. The low level of limonene is important because the amounts of limonene called for by this reference may be unsuitable for many oral applications. Significantly, also, the invention contains extremely low amounts of pulegone, a compound in mint with toxicity concerns (Nelson, S. (1995) "*Mechanisms of the formation and disposition of reactive metabolites that can cause acute liver injury*" Drug Metab Rev. 27 (1-2):147-177).

According to the invention, a preferred process of preparing the adjuvant compositions of the invention will comprise: obtaining a steam distilled flavor fraction from dried mint leaves, and isolating a low-boiling fraction of said steam distilled flavor fraction. The steam distilled flavor fraction is preferably made by subjecting sun-dried mint leaves to direct steam heat and then fractionating the resulting fraction to recover a low-boiling fraction. Desirably, the mint is mowed just prior to flowering and allowed to wilt in the sun. Any of the various species of mint can be employed, including all of those from the mint family of herbs, botanical family name Labiatae, which encompasses multiple genera including *Rosmarinus* (rosemary), *Monarda* (horsemint) and *Mentha* (mint). Common mint species include *Mentha piperita* (peppermint), *Mentha spicata* (spearmint), *Mentha arvensis* (cornmint) and *Mentha pulegium* (pennyroyal).

According to the preferred process of preparation, the steam distilled flavor fraction (sometimes called crudely distilled mint oil) is subjected to fractional distillation by indirect heat (e.g., conveniently steam) at vacuum pressure. This can be accomplished by feeding the crudely distilled mint oil to a fractionating column with structured packing/trays wherein the crudely distilled mint oil is subjected to an external heat source, and a progressive vacuum is applied. The distillation is preferably carried out at temperatures ranging from 0° C. (or ambient) to boiling point, and the fraction of interest elutes within a temperature range of 0-185° C., i.e., at 185° C. and below. The distillation is preferably performed under vacuum with pressures starting at atmosphere and decreasing progressively toward 1 mm Hg by the end of the process. The fractions of greatest interest elute at pressures between 760 and 100 mm Hg and at temperatures of 50-185° C. Preferably, the fractions are collected at elution rates of 0.1 to 10 kg/min in increments of 1-4% of the starting volume, and the individual fractional by-products in the low boiling range from the distillation are bulked together to make uniform batches in a manner that meets a preferred adjuvant composition specification. In a highly preferred form, the VDMO is a light boiling fraction isolated from Peppermint Oil, *Mentha piperita*, by vacuum distillation. The VDMO is collected under distillation conditions where the vacuum is being increased during the early stages of the process. Beginning at atmospheric pressure (760 mm Hg) and increasing the vacuum to 100 mm Hg, the fraction would be recovered according to the following boiling point range, 40-44° C. at 760 mm Hg to 35-40° C. at 100 mm Hg.

In one aspect, the present invention provides a component of mint oil, comprised of a fraction that is not specifically known or utilized as such in food systems, either as a flavor or as a food. In another aspect the invention provides a fraction derived from mint oil, comprising a mixture of terpene hydrocarbons, the oxygenated terpene 1,8-cineole, various aldehydes (2- and 3-methylbutanal, 2-methylpropanal, etc.), alcohols, ketones, and alkanes. The invention does not contain the concentrations of menthol, menthone and derivatives found in very refined mint products. The invention is also characterized by a mixture of polar and nonpolar compounds which function together to increase bioavailability.

It is an advantage of the invention that it promotes the uptake and absorption of numerous natural and synthetic compounds; the efficacy of the invention for the promotion of bioavailability depends on the ability of the compound to be solubilized by the invention. Various experimental methods have been used to demonstrate that the described invention increases the bioavailability of bioactive compositions, such as CoQ10. In vitro absorption/bioavailability is demonstrated in cultured human gut cells and it is demonstrated that cells accumulate more CoQ10 in the presence of the invention. It is further demonstrated that cultured human gut cells transport greater amounts (in a dose-dependent fashion) of CoQ10 from the apical to basolateral sides of a cell monolayer in the presence of the invention.

Very significantly, the invention has been shown in adult mice to increase the oral bioavailability of CoQ10, also in a dose dependent fashion. Oral bioavailability of CoQ10 is enhanced by the presence of the invention, relative to CoQ10 in an aqueous solution. As soybean oil is often used in the industry as a carrier for CoQ10, oral bioavailability of CoQ10 mixed with the invention has been compared to CoQ10 in soybean oil, and superior bioavailability as has been noted.

Moreover, the ultimate goal of CoQ10 supplementation is to increase CoQ10 concentrations at the site of metabolism within a tissue. The compositions of the present invention can increase the concentration of CoQ10, in a dose-dependent fashion, in the mitochondria of mammals as shown in tests on the livers of mice. Preferred compositions are effective to enhance delivery of CoQ10 to the interior cellular environment, including organelles, such as the mitochondria.

A preferred adjuvant composition specification will provide for a ratio (by weight) of nonpolar compounds and compounds with some polar characteristics within the range of from 5:1 to 20:1. In a preferred form the nonpolar compounds comprise compounds selected from a group that includes terpene hydrocarbons and terpene derivatives and the compounds with some polar characteristics comprise compounds selected from a group that includes aldehydes, alcohols and ketones. Compositionally, a preferred adjuvant composition will comprise less than 10% limonene, less than 5% of any of menthol, menthone, menthofuran, menthyl acetate and germacrene D. These are principal flavor ingredients of mint oil and may be too strong in the final adjuvant composition if not reduced to less than 10% of their initial values in the crudely distilled mint oil. It will also preferably contain less than 1% of any of pulegone, menthyl acetate, and germacrene-d. Also, desirably, the adjuvant composition will preferably contain between 1 and 30% of at least two of α-pinene, β-pinene, sabinene and 1,8-cineole, while also containing measurable amounts of at least two of myrcene, para-cymene, farnesene, neo-menthol, 1-octen-3-ol, 3-octanol, and viridiflorol. The preferred adjuvant compositions will also contain at least 0.5% by weight of at least two of the following nonpolar substances: myrcene, farnesene and para-cymene. Preferred compositions will contain a diverse mixture of compounds found in the essential oil of mint; such compounds include terpene hydrocarbons, oxygenated terpenes, aldehydes, alcohols, ketones, and alkanes, and will contain both polar and nonpolar molecules.

The invention will be exemplified below with specific emphasis on improving the absorptivity of bioactive compositions by exemplifying compositions containing Coenzyme Q10 (ubiquinone; CoQ10) but is fully applicable to a variety of other such bioactive compositions, including by way of example, compositions selected from the group consisting of Coenzyme Q10 (ubiquinone; CoQ10), carotenoids (e.g., β-carotene), curcuminoids, lycopene, resveratrol, Flavonoids and other phenolic compounds, organosulfur compounds, saponins, sterols, stanols, mixtures of at least two of these, and the like.

The adjuvant compositions of the invention will be used in any suitable dosage form along with a desired bioactive composition. They can be used in liquid form as the extract is prepared, in a solvent or as a dry powder. In a preferred liquid form they will comprise along with the desired bioactive composition as the liquid emulsion into a gel-cap, pill, capsule, soft-center gum or confection. The compositions of the invention can also be utilized as a powder for tableting, encapsulation or addition to food or beverages. In the case of CoQ10, the adjuvant will preferably be present at a weight to weight ratio of adjuvant to CoQ10 of from 1:1 to 5:1, and preferably at a ratio of about 2.5:1.

It is an advantage of the invention that the new adjuvant compositions are characterized by the ability to increase permeability of desired bioactive compositions, including CoQ10, though a layer of intestinal epithelial cells in culture. They are further characterized by the ability to increase uptake of desired bioactive compositions by intestinal epithelial cells in culture and are effective in the maintenance of normal levels of desired bioactive compositions circulating in the body by acting as an adjuvant for orally administered desired bioactives, such as Coenzyme Q10. Also, importantly, the adjuvant compositions of the invention are preferably characterized by the ability to improve uptake and/or trans-cellular movement of a dissolved bioactive composition by intestinal epithelial cells in culture. Significantly, the adjuvant compositions of the invention can improve delivery of the bioactive ingredients to cellular organelles.

The following examples are presented to further explain and illustrate the invention and are not to be taken as limiting in any regard. Unless otherwise indicated, all parts and percentages are by weight.

Example 1

Distillation and Isolation of the Low-Boiling Fraction of Mint Oil Derived from a Steam Distillate of Dried Mint Leaves A suitable species of mint is cultivated under appropriate conditions for an appropriate time. The mint is mowed just prior to flowering and allowed to wilt in the sun before being subjected to steam distillation in the field. The resultant distillate, termed the 'crude mint oil' is transported to a facility where it may be used immediately for some applications or subjected to further distillation for other uses.

The invention is produced when the crude mint oil is further distilled to separate the 'low-boiling' component from the more desirable flavor molecules such as menthol, menthone, menthofuran and menthyl acetate. The crude mint oil is subjected to indirect heat in a boiler connected to a 30' fractionating column. The heat is increased slowly from 0° C. to the boiling point concurrently with an increase in vacuum pressure from atmosphere to 1 mm Hg by the end of the process. The substances that are volatilized are condensed and collected in discrete fractions determined by the specific application. For the present application the fraction volatilized between 50-185° C., under a vacuum of 760-1 mm Hg is collected in increments of 1-4% of the starting volume and at elution rates of 0.1-10 kg/min. Individual fractions are analyzed by gas chromatography and suitable fractions are recombined to form a product that meets the pre-determined specification.

Multiple distillation processes were run and resulted in multiple VDMO compositions. These compositions were analyzed and only compositions that met a specification of less than 5% limonene, less than 10% collectively of menthol, menthone, menthofuran and menthyl acetate and less than 1% pulegone were studied for enhancement of bioavailability.

Example 2

Mint oils vary in composition, and subsequent distillation can be used to generate VDMO fractions with distinct compositions. The ranges of some of the common constituents of the crude oils cornmint (*Mentha arvensis*), peppermint (*Mentha piperita*) and spearmint (*Mentha spicata*) are shown in Table 1.

TABLE 1

Exemplary composition of some important components of the crude oil of selected mint species.

| Component | CAS # | Peppermint oil | Cornmint Oil | Spearmint Oil |
|---|---|---|---|---|
| Carvone | 2244-16-8 | — | — | 55.0-70.0 |
| 1,8-Cineole | 470-82-6 | 2.0-6.0 | 0.1-0.5 | 1.0-4.0 |
| l-Limonene | 5989-27-5 | 1.0-4.0 | 1.0-4.0 | 15.0-25.0 |
| Linalool | 78-70-6 | trace | 0.1-0.5 | 0.1-0.5 |
| l-Menthol | 15356-70-4 | 30.0-45.0 | 45.0-75.0 | trace |
| Menthone | 10458-14-7 | 19.0-25.0 | 10.0-20.0 | 1.0-4.0 |
| Menthofuran | 494-90-6 | 1.0-6.0 | trace | 0.5-1.0 |
| Menthyl Acetate | 16409-45-3 | 3.0-10.0 | 4.0-8.0 | — |
| Myrcene | 123-35-3 | 0.1-0.5 | 0.5-1.5 | 0.5-1.0 |
| Neomenthol | 3623-51-6 | 2.0-6.0 | 1.0-3.0 | 0.01 |
| 1-Octen-3-ol | 3391-86-4 | | | |
| 3-Octanol | 589-98-0 | | | |
| α-Pinene | 80-56-8 | 0.5-1.0 | 0.5-1.0 | 0.8 |
| β-Pinene | 127-91-3 | 0.5-1.0 | 0.5-1.0 | 0.8 |
| Pulegone | 89-82-7 | 0.5-1.0 | 0.5-1.0 | — |
| trans-Sabinene hydrate | 546-79-2 | 0.5-1.0 | 0.1-0.5 | 0.1-0.5 |
| Sabinene | 3387-41-5 | 0.5-1.0 | 0.1-0.5 | 0.1-0.5 |
| α-Terpineol | 98-55-5 | 0.1-0.5 | trace | 0.1-0.5 |
| α-Terpinene | 99-86-5 | 0.1-0.5 | — | — |

Mint oils may be further fractionated to yield oils with very different analyses. Table 2 shows the compositions of different mint oils that have been further distilled according to different parameters; the compositions are of the components that were left after the favorable flavor components have been separated.

TABLE 2

Exemplary composition of selected VDMO fractions produced by removing favorable flavor compounds

| VDMO fraction | | Composition by G.C. (% area) | | | | |
|---|---|---|---|---|---|---|
| Lot | CAS # | b | C | d | e 1 | e 2 | e 3 |
| β-Bourbonene | 5208-59-3 | | <1.0 | | 0.02 | 0.02 | |
| Cadinene | 29350-73-0 | | | | | 0.02 | |
| l-Carveol | 99-48-9 | | 0.02 | | | | |
| l-Carvone | 99-49-0 | 0.23 | 0.10 | | 1.20 | 0.88 | |
| l-Carvyl acetate | 97-42-7 | | 0.01 | | | | |
| Caryophyllene | 87-44-5 | 0.04 | 0.24 | | 0.04 | 0.09 | |
| l-Citronellal | 5949-05-3 | | | | | | |
| 1,8-Cineole | 470-82-6 | 28.34 | 26.12 | 9.87 | 10.52 | 10.69 | 0.09 |
| p-Cymene | 99-87-6 | 0.54 | 0.72 | 0.62 | 0.34 | 0.38 | |
| Decanal | 112-31-2 | | | | | | |
| Dimethyl styrene | 1195-32-0 | 0.03 | | | 0.12 | 0.02 | 0.01 |
| 2,5-Diethyl tetrahydrofuran | 41239-48-9 | | | | 0.15 | 0.45 | 2.75 |
| 2-Ethylfuran | 3208-16-0 | | | | 0.32 | 0.30 | |
| Ethyl-2-methyl butyrate | 7452-79-1 | 0.16 | 0.14 | | 0.05 | 0.33 | |
| trans-β-Farnesene | 502-61-4 | | | 0.86 | | | |
| Germacrene-D | 23986-74-5 | 0.03 | 0.20 | | 0.03 | 0.08 | |
| 1-Hexen-3-ol | 4798-44-1 | | | | 0.12 | 0.25 | 1.27 |
| cis-3-Hexenol | 928-96-1 | 0.21 | 0.25 | | 0.05 | 0.33 | 4.16 |
| trans-2-Hexenol | 928-95-0 | | | | | | |
| trans-2-Hexenal | 6728-26-3 | | | | | 0.04 | |
| d,l-Isomenthone | 491-07-6 | 0.12 | 0.57 | 0.32 | 0.20 | 0.35 | |
| Isopulegol | 89-79-2 | | 0.27 | | | | |
| Isovaleraldehyde | 590-86-3 | 0.38 | 1.24 | | 0.07 | 0.21 | |
| Jasmone | 488-10-8 | | 0.02 | | | | |
| l-Limonene | 5989-54-8 | 8.04 | 10.58 | 4.80 | 7.97 | 7.55 | 0.03 |
| Linalool | 78-70-6 | 0.08 | 0.07 | | 0.04 | 0.07 | 0.05 |
| Menthofuran | 494-90-6 | 0.12 | 1.59 | 0.40 | 0.06 | 0.08 | |
| l-Menthol | 89-78-1 | 0.81 | 1.73 | 1.22 | 0.52 | 1.33 | |
| Menthone | 89-80-5 | 0.86 | 7.02 | 2.67 | 0.70 | 1.27 | |
| Menthyl acetate | 89-48-5 | 0.07 | 0.15 | 0.11 | 0.04 | 0.14 | |
| 2-Methyl butanal | 96-17-3 | | | | 0.61 | 0.45 | |
| 2-Methylpropanal | 78-84-2 | | | | 0.08 | 0.06 | 0.02 |
| Myrcene | 123-35-3 | 2.32 | 2.02 | 2.15 | 4.29 | 4.57 | 0.21 |
| Neomenthol | 20752-34-5 | 0.06 | 0.27 | 0.14 | 0.05 | 0.11 | |
| cis-β-Ocimene | 3338-55-4 | 0.53 | 1.23 | 0.50 | | | |
| trans-β-Ocimene | 13877-91-3 | | | | | 0.03 | |
| 3-Octanol | 589-98-0 | 0.33 | 0.76 | 0.50 | 1.39 | 1.35 | 0.08 |
| 3-Octanol acetate | 8008-79-5 | 0.13 | 0.03 | | | 0.03 | |
| 1-Octen-3-ol | 3391-86-4 | 0.20 | 0.53 | 0.70 | 0.22 | 1.40 | 0.03 |
| α-Pinene | 80-56-8 | 17.40 | 11.55 | 31.80 | 18.83 | 19.71 | 71.10 |
| β-Pinene | 127-91-3 | 20.31 | 12.07 | 21.40 | 29.31 | 23.64 | 10.37 |
| Piperitone | 89-81-6 | 0.04 | 0.03 | | | 0.06 | |
| Pulegone | 89-82-7 | 0.04 | 0.05 | | 0.03 | 0.12 | |
| Sabinene hydrate | 546-79-2 | 0.12 | 0.51 | | 0.16 | 0.09 | |
| Sabinene | 3387-41-5 | 8.77 | 5.50 | 10.55 | 14.79 | 12.23 | 5.26 |
| α-Terpinene | 99-86-5 | 2.73 | 2.86 | 1.15 | | | |
| γ-Terpinene | 99-85-4 | | | | 0.28 | 0.32 | |
| γ-Terpinenol | 586-81-2 | 1.02 | 3.06 | 1.23 | | | |
| Terpinolene | 586-62-9 | | | | 0.26 | 0.24 | 0.35 |
| α-Terpineol | 98-55-5 | | 0.01 | | 1.08 | 0.91 | 0.02 |
| 4-Terpinenol | 562-74-3 | 0.05 | 0.24 | | 0.07 | 0.08 | |
| Viridiflorol | 552-02-3 | 0.04 | 0.15 | 0.02 | 0.05 | | |
| Total | | 94.19 | 92.04 | 91.13 | 93.96 | 90.57 | 95.79 |

Specific fractions and/or lots can be obtained that meet specific criteria. Criteria of less than 5% limonene, less than 5% menthol, menthone, and menthofuran (each), less than 1% each of pulegone, menthyl acetate, and germacrene-d, between 1 and 30% of at least two of α-pinene, β-pinene, sabinene and 1,8 cineole and containing measurable amounts of at least two of myrcene, para-cymene, farnesene, neomenthol, 1-octen-3-ol, 3-octanol, and viridiflorol were set. Two specific VDMO lots that met these criteria were analyzed more completely by GC-mass spec; the results are shown in Table 3a also categorizes the compounds according to polarity, and shows that this VDMO fraction is between 5:1 and 20:1 ratio of nonpolar:polar compounds. Table 3b summarizes GC-mass spec analyses of the VDMO fraction utilized in bioavailability experiments; substances are classified by polarity. This VDMO is a light boiling fraction isolated from Peppermint Oil, Mentha piperita, by vacuum distillation. The VDMO was collected under distillation conditions where the vacuum was being increased during the early stages of the process. Beginning at atmospheric pressure (760 mm Hg) and increasing the vacuum to 100 mm Hg, the fraction was recovered according to the following boiling point range, 40-44° C. at 760 mm Hg to 35-40° C. at 100 mm Hg.

This embodiment of VDMO of the invention was used in subsequent bioavailability experiments.

TABLE 3a

GC-mass spec ranges of VDMO fraction utilized in bioavailability experiments

| | | VDMO | Polarity | | |
|---|---|---|---|---|---|
| Substance | CAS # | composition (range %) | non | moderately | extremely |
| Amyl alcohol | 71-41-0 | Trace 1.0 | | x | |
| Caryophyllene | 87-44-5 | Trace 1.0 | x | | |
| 1,8 Cineole | 470-82-6 | 1.0 5.0 | x | | |
| 2-Ethylfuran | 3208-16-0 | Trace 1.0 | x | | |
| Ethyl-2-methyl butyrate | 7452-79-1 | Trace 1.0 | | x | |
| Germacrene-D | 23986-74-5 | Trace 1.0 | | x | |
| cis-3-Hexenol | 928-96-1 | 0.1 2.0 | | x | |
| trans-2 Hexen-1-ol | 928-95-0 | Trace 1.0 | | x | |
| trans-2-Hexenal | 6728-26-3 | Trace 1.0 | | x | |
| l-Limonene | 5989-54-8 | 1.0 5.0 | x | | |
| Linalool | 78-70-6 | Trace 1.0 | | x | |
| Menthofuran | 494-90-6 | < 1.0 | x | | |
| l-Menthol | 89-78-1 | < 5.0 | | | x |
| l-Menthone | 89-80-5 | < 5.0 | | | x |
| l-Menthyl acetate | 89-48-5 | < 1.0 | x | | |
| 2-Methyl butanal | 96-17-3 | Trace 1.0 | | x | |
| 3-Methyl-1-butanal | 590-86-3 | Trace 1.0 | | x | |
| 2-Methyl-1-butanol | 137-32-6 | Trace 1.0 | | x | |
| 3-Methyl-1-butanol | 123-51-3 | Trace 1.0 | | x | |
| 2-Methylpropanal | 78-84-2 | Trace 1.0 | | x | |
| Myrcene | 123-35-3 | 1.0 5.0 | x | | |
| cis-β-Ocimene | 3338-55-4 | Trace 1.0 | x | | |
| 3-Octanol | 589-98-0 | Trace 1.0 | | x | |
| 1-Octen-3-ol | 3391-86-4 | Trace 1.0 | | x | |
| α-Pinene | 80-56-8 | 10.0 30.0 | x | | |
| β-Pinene | 127-91-3 | 10.0 30.0 | x | | |
| Piperitone | 89-81-6 | Trace 1.0 | | x | |
| Pulegone | 89-82-7 | < 1.0 | | | x |
| Sabinene hydrate | 546-79-2 | Trace 1.0 | | x | |
| Sabinene | 3387-41-5 | 10.0 30.0 | x | | |
| Spathulenol | 6750-60-3 | Trace 1.0 | | x | |
| α-Thujene | 3917-48-4 | 1.0 5.0 | x | | |
| γ-Terpinene | 99-85-4 | 1.32 0.08 | x | | |
| Terpinolene | 586-62-9 | Trace 1.0 | x | | |
| Viridiflorol | 552-02-3 | Trace 1.0 | | x | |
| Total polar compounds | | 11.62 9.15 | | | |

TABLE 3b

GC-mass spec analyses of VDMO fraction utilized in bioavailability experiments; substances are classified by polarity.

| Substance | CAS # | VDMO composition | | Polarity non | moderately | extremely |
|---|---|---|---|---|---|---|
| Amyl alcohol | 71-41-0 | 0.33 | 0.73 | | x | |
| Caryophyllene | 87-44-5 | 0.05 | 0.08 | x | | |
| 1,8-Cineole | 470-82-6 | 9.77 | 4.28 | x | | |
| p-Cymene | 99-87-6 | 0.43 | 0.27 | x | | |
| Decanal | 112-31-2 | | 0.06 | | x | |
| Dihydro carvone | 7764-50-3 | | 0.05 | | | x |
| p-α-Dimethyl styrene | 1195-32-0 | 0.16 | | x | | |
| 2,5-Diethyl tetrahydrofuran | 41239-48-9 | 0.75 | | x | | |
| Elemol | 639-99-6 | 0.06 | | | x | |
| Ethanol | 64-17-5 | 0.03 | | | | x |
| 2-Ethylfuran | 3208-16-0 | 0.34 | 0.11 | x | | |
| Ethyl-2-methyl butyrate | 7452-79-1 | 0.10 | 0.23 | | x | |
| trans-β-farnesene | 502-61-4 | | 0.02 | x | | |
| Germacrene-D | 23986-74-5 | 0.09 | 0.05 | | x | |
| 1-Hexen-3-ol | 4798-44-1 | 0.47 | | | x | |
| cis-3-Hexenol | 928-96-1 | 0.61 | 1.14 | | x | |
| trans-2 Hexen-1-ol | 928-95-0 | 0.35 | 0.02 | | x | |
| trans-2-Hexenal | 6728-26-3 | 0.11 | 0.07 | | x | |
| Isopulegol | 89-79-2 | | 0.02 | | x | |
| Jasmone | 488-10-8 | | 0.02 | | x | |
| l-Limonene | 5989-54-8 | 4.78 | 3.39 | x | | |
| Linalool | 78-70-6 | 0.08 | 0.09 | | x | |
| Menthofuran | 494-90-6 | 0.40 | | x | | |
| l-Menthol | 89-78-1 | 1.25 | 0.52 | | | x |
| Menthone | 89-80-5 | 2.66 | 0.45 | | | x |
| Menthyl acetate | 89-48-5 | 0.11 | 0.08 | | x | |
| 2-Methyl butanal | 96-17-3 | 0.69 | 0.21 | | x | |
| 3-Methyl-1-butanal | 590-86-3 | 0.87 | 0.32 | | x | |
| 2-Methyl-1-butanol | 137-32-6 | 0.37 | 1.73 | | x | |
| 3-Methyl-1-butanol | 123-51-3 | 0.45 | 2.00 | | x | |
| 2-Methylpropanal | 78-84-2 | 0.23 | 0.02 | | x | |
| Myrcene | 123-35-3 | 2.28 | 2.92 | x | | |
| Neomenthol | 20752-34-5 | 0.14 | | | | x |
| cis-β-Ocimene | 3338-55-4 | 0.53 | 0.01 | x | | |
| trans-β-Ocimene | 13877-91-3 | 0.14 | | x | | |
| 3 Octanol | 589-98-0 | 0.46 | 0.57 | | x | |
| 3-Octanol acetate | 8008-79-5 | 0.32 | | | x | |
| 1-Octen-3-ol | 3391-86-4 | 0.23 | 0.05 | | x | |
| α-Pinene | 80-56-8 | 31.92 | 26.90 | x | | |
| β-Pinene | 127-91-3 | 21.58 | 31.76 | x | | |
| Piperitone | 89-81-6 | 0.02 | 0.05 | | x | |
| Pulegone | 89-82-7 | 0.02 | 0.09 | | | x |
| Sabinene hydrate | 546-79-2 | 0.07 | 0.02 | | x | |
| Sabinene | 3387-41-5 | 10.65 | 14.92 | x | | |
| Spathulenol | 6750-60-3 | 0.03 | 0.03 | | x | |
| α-Thujene | 3917-48-4 | 2.15 | 0.46 | x | | |
| α-Terpinene | 99-86-5 | | 0.16 | x | | |
| γ-Terpinene | 99-85-4 | 1.32 | 0.08 | x | | |
| Terpinolene | 586-62-9 | 0.58 | 0.25 | x | | |
| α-Terpineol | 98-55-5 | 1.34 | | | x | |
| 4-Terpinenol | 562-74-3 | | 0.01 | | x | |
| Viridiflorol | 552-02-3 | 0.14 | 0.10 | | x | |
| Total | | 99.44 | 94.73 | | | |
| Total polar compounds (%) | | 11.62 | 9.15 | | | |

Example 3

In Vitro Characterization of the Enhancement of CoQ10 Bioavailability by the Invention An initial pilot study established that VDMO improved the uptake of CoQ10 into Caco-2 cells. Caco-2 cells were grown for 15 days in the bottom of 24-well plastic culture dishes and then were exposed to 1 millimolar concentrations of CoQ10 mixed with 5%, 1% or no VDMO. The VDMO utilized here was as analyzed in Table 3b. Cells were returned to the incubator for two hours, then cells and media were separated by centrifugation. The cellular fraction was washed and centrifuged a second time and the amount of CoQ10 inside the cells was determined by Liquid Chromatography Mass Spectrometry. The experiment was repeated twice; the absorption in the control group was set to 100% and treatments were compared accordingly; results are shown in Table 4.

TABLE 4

A pilot project establishes that a VDMO improves the uptake of CoQ10 into Caco-2 cells.

| Treatment | Experiment 1 Absorption (%) | Experiment 2 Absorption (%) |
|---|---|---|
| CoQ10 + no VDMO; Control | 100 ± 6.1 | 100 ± 0.3 |
| CoQ10 + 1.0% VDMO | 127 ± 4.7 | 129 ± 0.8 |
| CoQ10 + 5.0% VDMO | 165 ± 6.2 | 176 ± 4.0 |

The percent absorption, as determined by uptake of CoQ10 into Caco-2 cells, was set at 100% for the control group Subsequent experiments utilized Caco-2 cells grown on porous membranes; cells were seeded ($1 \times 10^5$ cells) on Corning Transwell membranes inserts (24 mm radius, 0.4 µM pore size) in E-well plates with bi-cameral chambers; the cells were grown for 17 days to ensure polarization and formation of tight junctions. Culture media (High Glucose Dulbecco's Modified Eagle Medium (DMEM)+10% Fetal Bovine Serum (FBS)+penicillin/streptomycin) was changed every 3 days.

Experimental media (Table 5) containing different concentrations of VDMO, were prepared on the day of the experiment and were diluted in high glucose DMEM. Experiment 1 used media with FBS, experiment 2 did not contain serum. Experimental media also contained CoQ10, bile salts and Butylated Hydroxy Toluene (BHT) to prevent oxidation. Micelle formation was facilitated by five minutes of sonication.

TABLE 5

Composition of experimental media used for uptake and transcellular transport studies of CoQ10 in Caco-2 cells.

| VDMO (% of media) | CoQ10 Exp 1 (µM) | FBS | Bile salts (mM) | BHT (µM) | CoQ10 Exp 2 (µM) | FBS | Bile Salts (mM) | BHT Exp 2 (µM) |
|---|---|---|---|---|---|---|---|---|
| 3.0 | 12.9 | Yes | 0.04 | 50 | 23.0 | No | 2.4 | 90 |
| 1.0 | 12.9 | Yes | 0.04 | 50 | 23.0 | No | 2.4 | 90 |
| 0.5 | 12.9 | Yes | 0.04 | 50 | 23.0 | No | 2.4 | 90 |
| 0.005 (control) | 12.9 | Yes | 0.04 | 50 | 23.0 | No | 2.4 | 90 |

On the day of the experiment, old media were removed and 1.5 mL of the respective experimental media were added to the apical side of the cells inside the insert; 2.5 mL of growth media (with or without serum) were added to the basolateral side (well) of the cells. Membranes were replaced in the wells and plates were returned to the incubator for 4.5 hrs. Following incubation, media were removed from each well for CoQ10 analysis. Cells were extensively washed to remove any trace of adhering medium or CoQ10, released by treatment with trypsin, transferred to test tubes, centrifuged and washed multiple times. The cell pellet was removed and homogenized in phosphate buffered saline.

Samples were extracted into methanol:petroleum ether (1:1), brought to dryness under a stream of nitrogen and re-dissolved in methanol:chloroform (1:2). Samples were analyzed for CoQ10 by HPLC by using a modification of the analysis reported by Turunen, M. et al. (1999) "*Blood concentration of coenzyme Q(10) increases in rats when esterified forms are administered*" J. Nutr. 129 (12):2113-2118. Briefly 150×4.6 mm Allure C18 column (3 uM) was eluted by methanol-water (9:1) and a methanol-propanol-hexane (2:1:1) gradient. Raw data were adjusted for concentrations of CoQ10 in the experimental media and for total protein (in cells only). Six wells were used for each treatment.

FIG. 1 illustrates that VDMO resulted in a statistically-significant, dose-dependent change in the uptake of CoQ10 in media that did not contain serum. VDMO increased the uptake of CoQ10 by Caco-2 cells up to a concentration of 1% VDMO; at a concentration of 3% the uptake of CoQ10 into cells was inhibited, resulting in an uptake similar to that of cells exposed to 0.5% VDMO. The effect of treatment is significant at $p<0.0001$ by ANOVA. Values are Means+SEM. Different superscripts represent means significantly different from each other.

Figure 2:
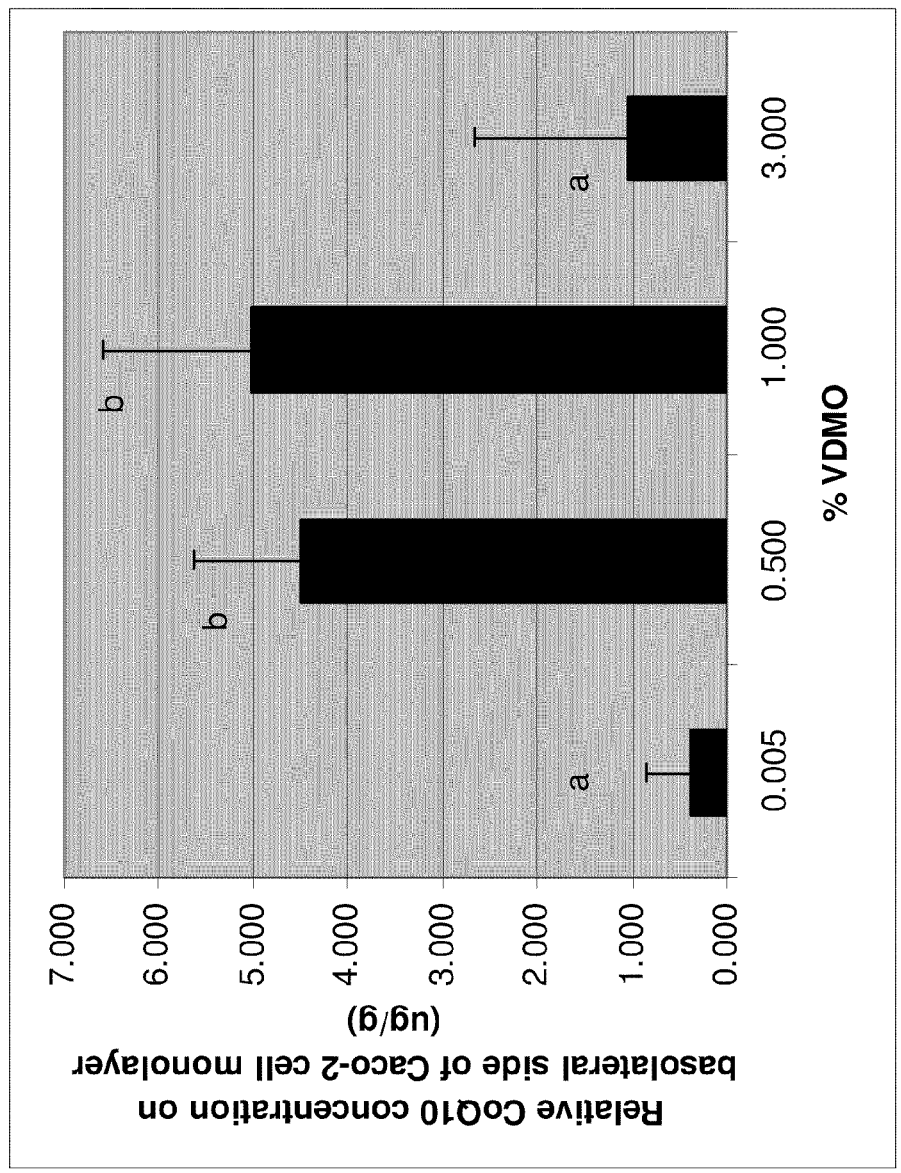
FIG. 2 is a graph showing that VDMO in serum-free media resulted in a statistically-significant, dose-dependent increase in the amount of CoQ10 that was transported across a monolayer of Caco-2 cells.

FIG. 2 illustrates that VDMO in serum-free media resulted in a statistically significant, dose-dependent increase in the amount of CoQ10 that was transported across a monolayer of Caco-2 cells; transport across Caco-2 cells is an in vitro indication of absorption and hence bioavailability. As with cellular uptake, transport across the monolayer increased up to a concentration of 1% VDMO. At a concentration of 3% the uptake of CoQ10 into cells was inhibited, resulting in an uptake similar to that of cells exposed to 0.5% VDMO. The effect of treatment is significant at $p<0.0001$ by ANOVA. Values are Means+SEM. Different superscripts represent means significantly different from each other.

Figure 3:
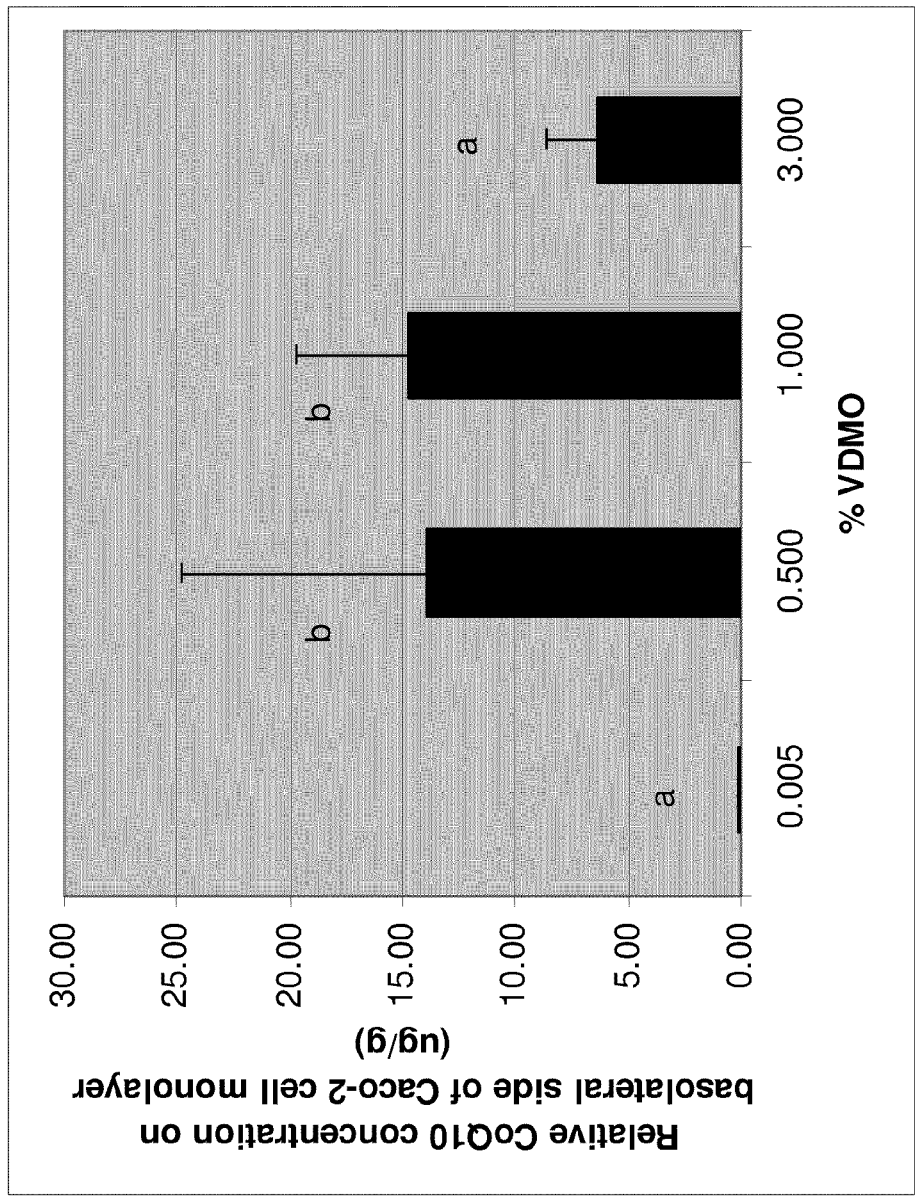
FIG. 3 is a graph showing that VDMO in media containing serum also resulted in a statistically significant, dose-dependent increase in the amount of CoQ10 that was transported across a monolayer of Caco-2 cells.

FIG. 3 illustrates that VDMO in media containing serum also resulted in a statistically significant, dose-dependent increase in the amount of CoQ10 that was transported across a monolayer of Caco-2 cells; transport across Caco-2 cells is an in vitro indication of absorption. The pattern of the effect of VDMO was very similar to that seen in cells exposed to experimental medium without serum. Transport of CoQ10 across a monolayer of Caco-2 cells is dependent on the concentration of VDMO in experimental medium containing serum. The effect of treatment is significant at $p<0.0003$ by ANOVA. Values are Means+SEM. Different superscripts represent means significantly different from each other.

Example 4

This example illustrates that the invention mixed with CoQ10 and Tween 80 in a manner that forms an emulsion changes the kinetics of CoQ10 appearance in the serum of mice.

A pilot study used 20 g BLB-c male mice that were fed standard chow and gavaged at time 0 with one of three test solutions shown in Table 6.

TABLE 6

Formulation of test solutions administered to mice by gavage in a preliminary animal study.

| Trt | CoQ10 (µg) | MBS (µg) | Tween 80 (mg) |
|---|---|---|---|
| Neg control | 500 | 0 | 10.5 |
| VDMO emulsion 2:1 | 500 | 1000 | 10.5 |
| VDMO emulsion 5:1 | 500 | 2500 | 10.5 |

Doses were diluted in sufficient phosphate buffered saline to bring each to a total volume of 0.5 mL. An emulsion was facilitated by vortexing followed by sonication. Blood was taken at 30, 60, 270 and 540 minutes post-gavage and serum was obtained by centrifugation; there were 5 mice per treatment per timepoint. Serum collected from the animals was extracted and analyzed for CoQ10 as per the above.

Figure 4:
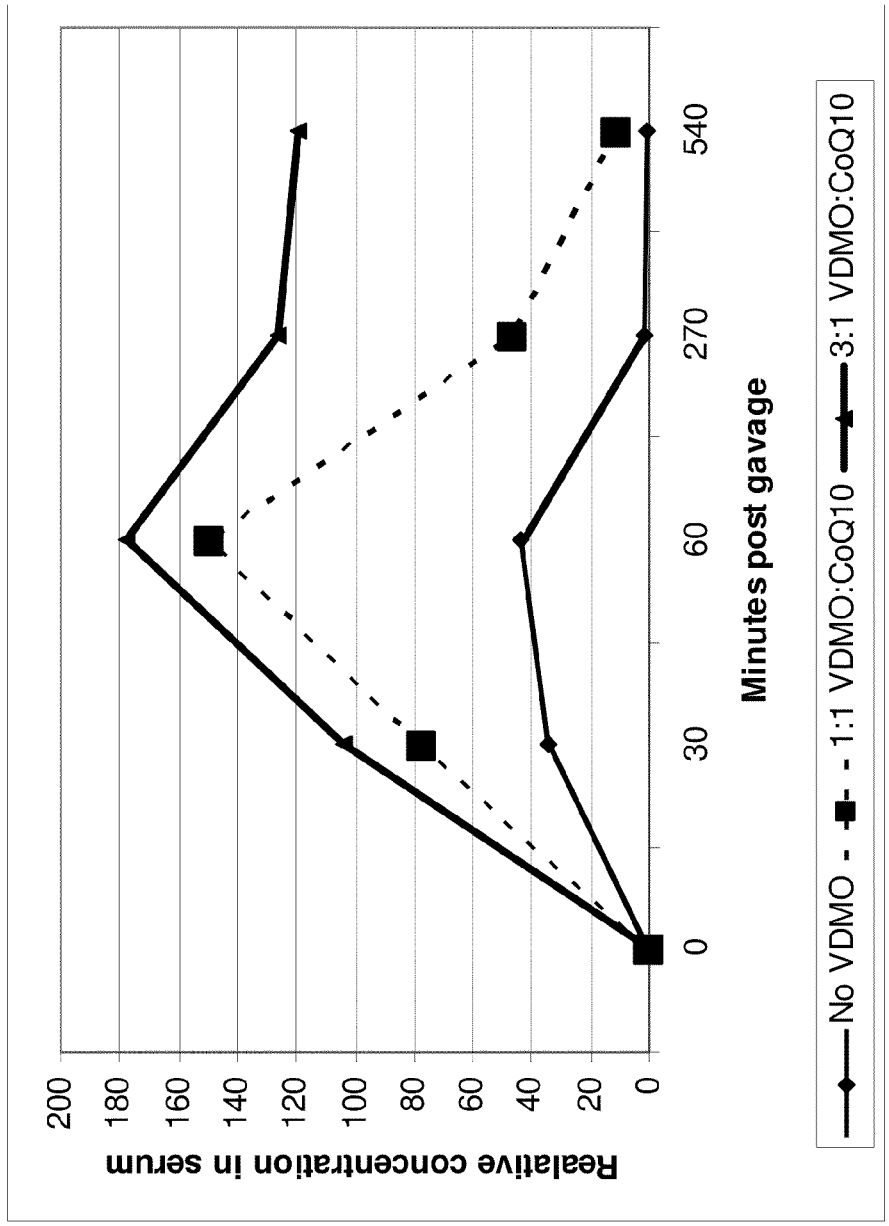
FIG. 4 is a graph showing preliminary data indicating that the kinetics of the appearance of CoQ10 in the serum of mice appears to change with the inclusion of the VDMO mixed with CoQ10 and Tween 80 in a manner that makes an emulsion.

FIG. 4 illustrates that preliminary data indicated that the kinetics of the appearance of CoQ10 in the serum of mice appear to change with the inclusion of the VDMO mixed with CoQ10 and Tween 80 in a manner that makes an emulsion.

The maximum peak height of CoQ10 appears to be increased in a dose-dependent manner by VDMO. In FIG. 4, each point is the mean of five measurements from different mice; data were not statistically analyzed.

Example 5

This example illustrates that the invention increases the bioavailability of CoQ10 to mice gavaged for 4 days with test solutions that contain CoQ10 and varying ratios of VDMO.

Fifteen 20 g BLB-c male mice, fed standard chow were gavaged at time 0 with the same treatments prepared in the same manner as for Example 4. After the initial gavage, animals were gavaged at 24 hour intervals for three additional consecutive days and killed the fourth day. Serum was collected and analyzed for CoQ10 as before.

Figure 5:
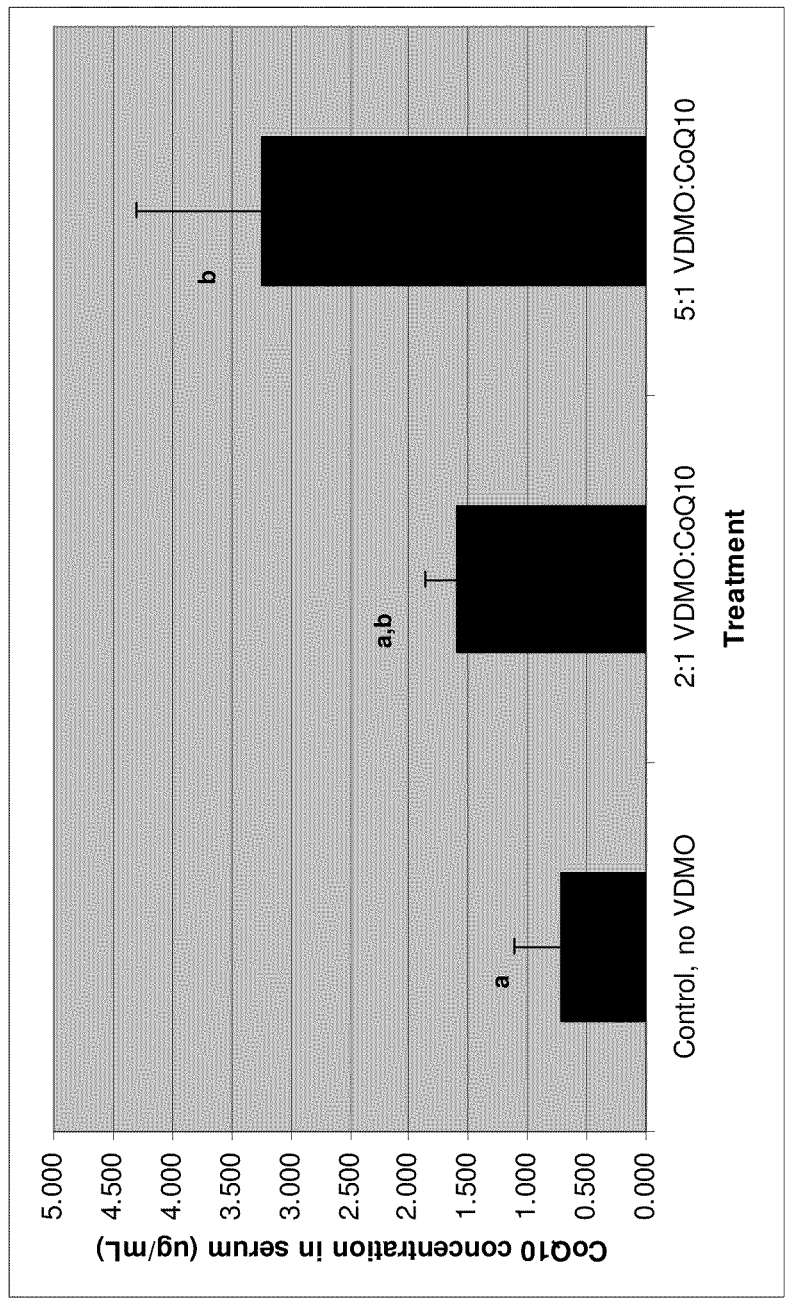
FIG. 5 is a graph showing that the concentration of CoQ10 in the serum of mice was significantly increased in a dose-dependent manner by VDMO.

FIG. 5 illustrates that the concentration of CoQ10 in the serum was increased in a dose-dependent manner by VDMO; this increase was statistically significant as determined by one-way Analysis Of Variance (ANOVA). The data were analyzed by one-way Analysis of Variance and the effect of treatment was significant at $p<0.05$. Data are Means with associated SEM; n=5 animals/treatment.

Example 6

This example illustrates that the invention increases the bioavailability of CoQ10 to mice gavaged with CoQ10 and varying ratios of VDMO or soybean oil for nine days. It further illustrates that the invention is superior to soybean oil as a bioavailability enhancer for CoQ10. Thirty-six 20 g BLB-c male mice, fed standard chow were gavaged daily for nine days with one of four treatments shown in Table 7.

TABLE 7

Composition of treatments administered by gavage to mice for nine days.

| Trt | CoQ10 (µg) | VDMO (µg) | Soybean oil (µg) | Tween 80 (mg) |
|---|---|---|---|---|
| Neg control | 500 | 0 | 0 | 10.5 |
| VDMO emulsion 2:1 | 500 | 1000 | 0 | 10.5 |
| VDMO emulsion 5:1 | 500 | 2500 | 0 | 10.5 |
| SB oil emulsion | 500 | 0 | 2500 | 10.5 |

As before, doses were formulated in phosphate-buffered saline to be a total of 0.5 mL.

Animals were gavaged at time 0 and at 24 hours thereafter for 9 consecutive days; animals were killed on the ninth day; serum prepared and analyzed for CoQ10 as before.

Figure 6:
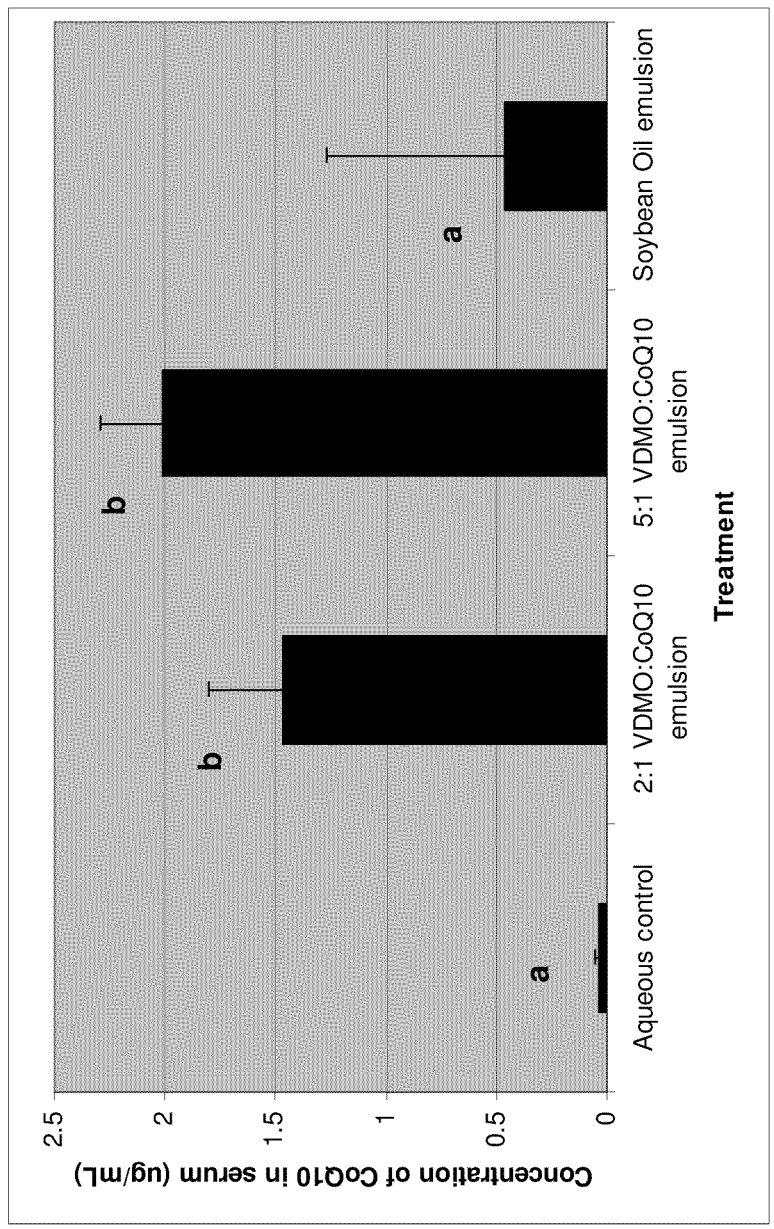
FIG. 6 is a graph showing that the VDMO significantly increased the concentration of CoQ10 in the serum of mice relative both to mice given the aqueous control as well as mice given the emulsion made with soybean oil.

FIG. 6 illustrates that the VDMO significantly increased the concentration of CoQ10 in the serum of mice relative to both mice given the aqueous control as well as mice given the emulsion made with soybean oil. For FIG. 6, the data are Means with associated SEM; n=8 or 9 per treatment; effect of treatment significant at $p<0.0001$ by one-way ANOVA; means with different superscripts are significantly different from each other.

Example 7

This example illustrates that the invention increases the concentration of CoQ10 in the mitochondrial fraction of liver cells of mice administered CoQ10 by gavage for nine consecutive days. As the mitochondria are involved in energy production and CoQ10 is a cofactor needed for energy production, concentration changes in this subcellular fraction are suggestive of a functional benefit.

The livers of mice used for Example 5 were excised and the mitochondrial fraction was obtained by homogenization in a mannitol/sucrose/HEPES buffer followed by differential centrifugation. The pellet obtained from the mitochondrial spin was rehomogenized and CoQ10 was analyzed as before.

Figure 7:
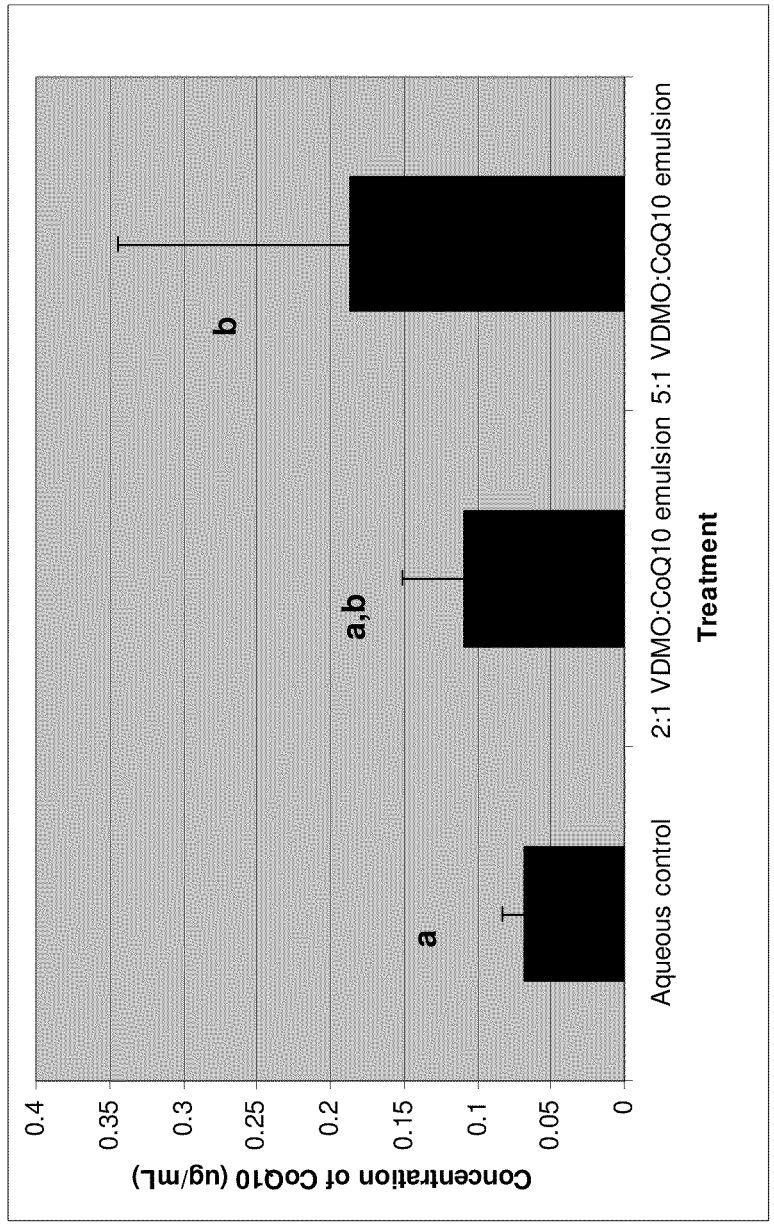
FIG. 7 is a graph showing that the invention caused a statistically significant increase in the concentration of CoQ10 in liver mitochondria.

FIG. 7 illustrates that the invention caused a statistically significant increase in the concentration of CoQ10 in liver mitochondria. FIG. 7 shows that the ratio of VDMO:CoQ10 alters the concentration of CoQ10 in the mitochondria of the liver of mice administered CoQ10 by gavage for nine consecutive days. Data are Means with associated SEM; n=8 or 9 per treatment; effect of treatment significant at $p=0.0653$ by one-way ANOVA; means with different superscripts are significantly different from each other.

Example 8

This example illustrates that the VDMO of the invention can be encapsulated in a gelatin capsule for a period of at least a month. The pure VDMO fraction was encapsulated for over a month in a soft gel capsule with no significant difference in shape or feel of the gelatin and no leaks.

The above description is for the purpose of teaching the person of ordinary skill in the art how to practice the invention. It is not intended to detail all of those obvious modifications and variations, which will become apparent to the skilled worker upon reading the description. It is intended, however, that all such obvious modifications and variations be included within the scope of the invention which is defined by the following claims. The claims are meant to cover the claimed components and steps in any sequence which is effective to meet the objectives there intended, unless the context specifically indicates the contrary.

The invention claimed is:

1. A process for preparing an adjuvant composition capable of increasing the bioavailability of a bioactive composition, comprising:
   a. subjecting dried mint leaves to direct steam heat to obtain a crude mint oil;
   b. heating said crude mint oil while applying and increasing a vacuum to volatilize and condense discreet fractions of said crude mint oil;
   c. collecting said discreet fractions of said crude mint oil and separating low-boiling fractions as byproduct fractions from higher boiling flavor fractions;
   d. analyzing the discreet byproduct fractions obtained in step c; and
   e. selecting and combining suitable byproduct fractions so as to obtain an adjuvant composition comprising less than 10% limonene and less than 5% of any of menthol, menthone, menthofuran, menthyl acetate and germacrene D.

2. A process according to claim 1 wherein, the mint leaves are obtained from mint that was mowed just prior to flowering and allowed to wilt in the sun.

3. A process according to claim 1, wherein the mint leaves are fraction is obtained from one or more mint species including *Mentha piperita* (peppermint), *Mentha* spicata (spearmint), *Mentha* arvensis (cornmint) and *Mentha* pulegium (pennyroyal).

4. A process according to claim 1, wherein the discrete fractions are collected in increments of 1-4% of the starting volume of the crude mint oil.

5. A process according to claim 1, wherein the adjuvant composition contains less than 1% of any of pulegone, menthyl acetate, and germacrene-d.

6. A process according to claim 1, wherein the adjuvant comprises a mixture of nonpolar compounds and compounds with polar characteristics.

7. A process according to claim 6, wherein the nonpolar compounds comprise compounds selected from the group consisting of terpene hydrocarbons and terpene derivatives and the compounds with polar characteristics comprise compounds selected from the group consisting of aldehydes, alcohols and ketones.

8. A process according to claim 6, wherein the weight ratio of nonpolar compounds and compounds with polar characteristics is within the range of from 5:1 to 20:1.

9. A process according to claim 6, wherein the adjuvant comprises at least 0.5% by weight of at least two of myrcene, farnesene and para-cymene as nonpolar compounds, and between 1 and 30% of at least two of α-pinene, β-pinene, sabinene and 1,8-cineole, and measurable amounts of at least two of myrcene, para-cymene, farnesene, neo-menthol, 1-octen-3-ol, 3-octanol, and viridiflorol.

* * * * *